United States Patent [19]

Okazaki

[11] Patent Number: 4,736,399

[45] Date of Patent: Apr. 5, 1988

[54] X-RAY IMAGING APPARATUS

[75] Inventor: Kiyoshi Okazaki, Tochigi, Japan

[73] Assignee: Kabushiki Kaisha Toshiba, Kawasaki, Japan

[21] Appl. No.: 763,226

[22] Filed: Aug. 7, 1985

[30] Foreign Application Priority Data

Aug. 8, 1984 [JP] Japan ................. 59-164843

[51] Int. Cl.⁴ .................... H05G 1/64; G06F 7/38; H04N 5/32
[52] U.S. Cl. ...................... 378/99; 378/98; 358/111; 358/110
[58] Field of Search ............ 378/99, 34, 35, 98; 358/111, 110; 364/414

[56] References Cited

U.S. PATENT DOCUMENTS

| | | | |
|---|---|---|---|
| 3,564,133 | 2/1971 | Hobrough | 358/88 |
| 4,212,061 | 7/1980 | Knoll et al. | 364/414 |
| 4,386,404 | 5/1983 | Knoll et al. | 364/414 |
| 4,549,208 | 10/1985 | Kamejima et al. | 358/108 |

Primary Examiner—Carolyn E. Fields
Assistant Examiner—Joseph A. Hynds
Attorney, Agent, or Firm—Finnegan, Henderson, Farabow, Garrett & Dunner

[57] ABSTRACT

An X-ray imaging apparatus irradiates an object with X rays radiated by an X-ray generator, converts an image of the object produced by X-rays transmitted through the object into an electrical signal, processes the X-ray image and visualizes the object image by a display unit. In the imaging apparatus, the amount of spatial coordinate distortion of the picked up image is measured from an image of an object before it is picked up and data representative of the distortion amount is stored in a distortion measuring unit. Addresses of pixels in the collected image, which correspond to the pixel addresses for storing the corrected image, are computed by an interpolating operation using the distortion data, and intensities of the pixels at the computed pixel addresses are computed, by the interpolating operation, from the pixel intensities in the collected image data.

9 Claims, 6 Drawing Sheets

F I G. 4
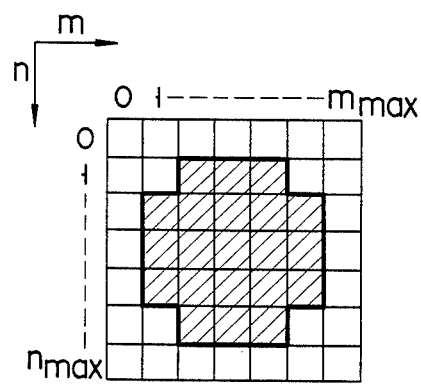

FIG. 5A
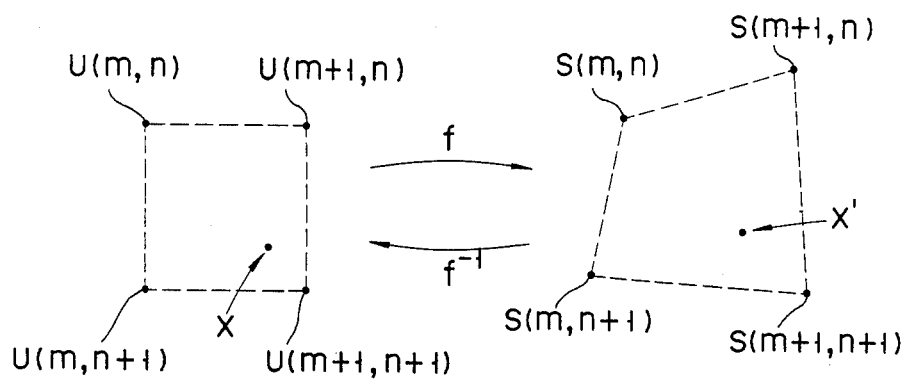
FIG. 5B
FIG. 6
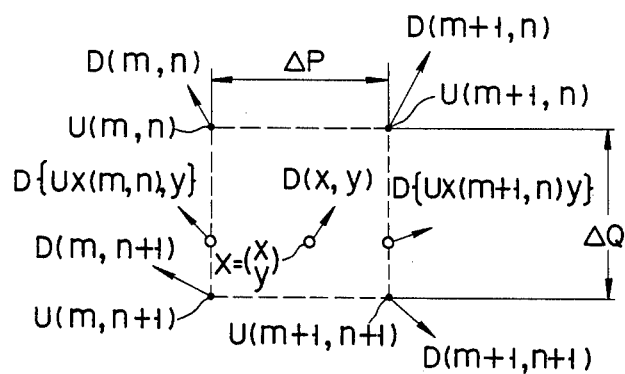
FIG. 7
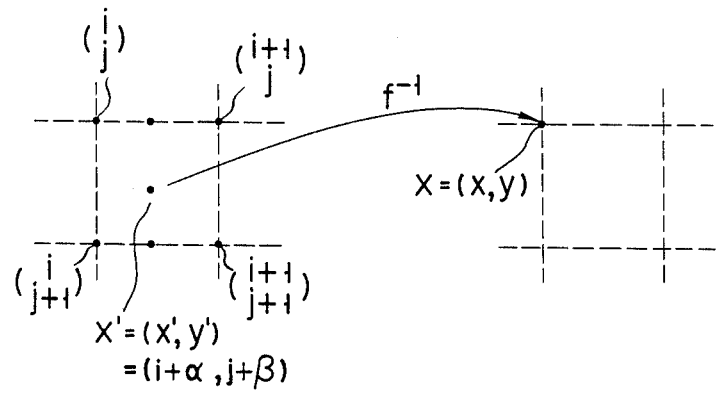

F I G. 9
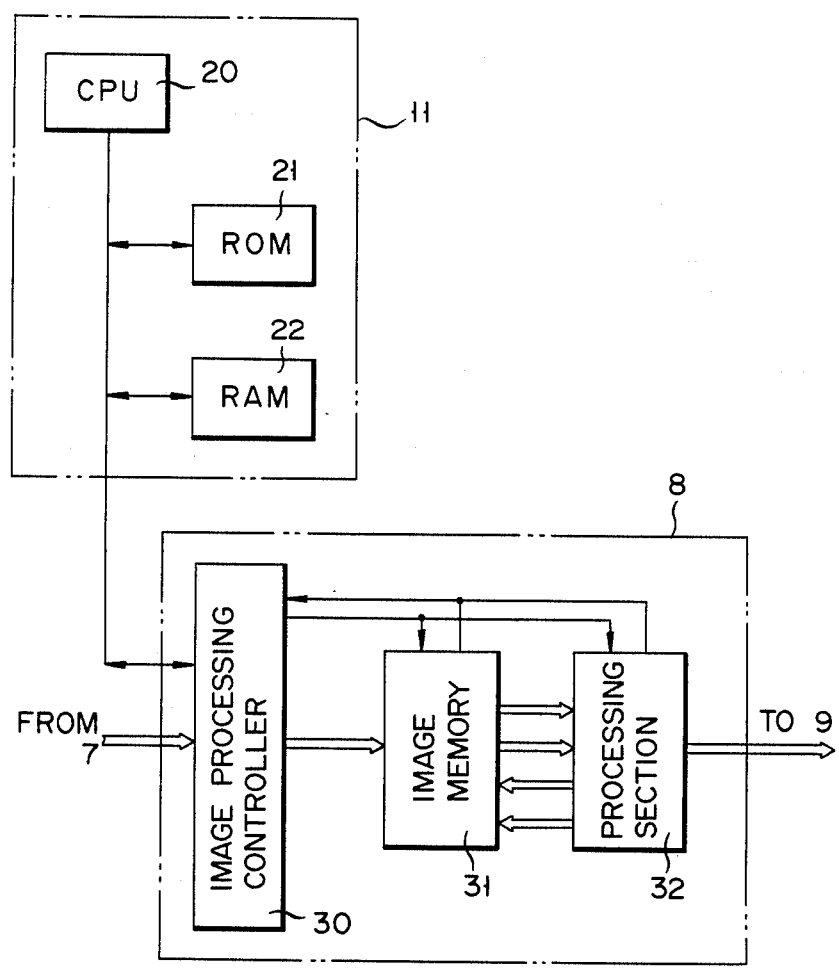

X-RAY IMAGING APPARATUS

BACKGROUND OF THE INVENTION

This invention relates to an X-ray imaging apparatus which detects X rays transmitted through an object, and produces an image or measured value effective for medical diagnosis or industrial inspection of the object.

A typical example of the conventional X-ray imaging apparatus is a digital fluorographic apparatus. The image visually displayed by such an apparatus inevitably suffers from spatial distortion caused by the detecting system of the imaging apparatus. (The detecting system contains an image intensifier (I.I.) for converting a detected X-ray image into an optical image, and a television camera for converting the optical image into corresponding electrical signals.) In an extreme case, the displayed image loses to a significant degree and due to spatial distortion its geometrical analogy to the configuration of the object. In some cases, contiguous aspects of the object are X-ray imaged so as to provide a series of images of contiguous aspects of the object. These segmental image frames are then composed to provide a composite image for observation. However, should each frame contain a large degree of spatial distortion the composite image will, likewise, be characterized by distortion, to the extent of its being an unnatural representation. Similarly, if in the X-ray tomographic apparatus or an X-ray stereoscopic imaging apparatus, the spatial distortion is contained in the X-ray transmission images before reconstruction, the reconstructed tomographic or stereoscopic image will be quite different in configuration from the object.

The inspection results or geometrical measurements based on such distorted images inevitably contain errors, resulting in imprecise diagnosis and/or inspection.

A recent trend in this field is the attempt to apply the X-ray imaging apparatus, the X-ray tomographic apparatus, the X-ray stereoscopic imaging apparatus and the like to analysis of heart volume, as well as to the exact measurement of a target position of an object. Such exact measurement is required for, for example, the operation of destroying renal calculus by means of an impact wave, radiotherapy or hyperthermia. Naturally, the existence of spatial distortion and the errors ensuing therefrom in a case where nothing short of a very precise measurement is called for creates serious problems.

SUMMARY OF THE INVENTION

Accordingly, an object of the present invention is to provide an X-ray imaging apparatus which can provide an image configured so as to closely approximate the original object by correcting the spatial distortion, thus realizing a display wherein the image suffers so little distortion that an exact quantitative inspection can reliably be based on it.

To achieve the above object there is provided an X-ray imaging apparatus having an X-ray generator for radiating X rays toward an object, means for detecting an image formed by X rays transmitted through the object to obtain first image data, an image processing means for applying a predetermined image processing to the first image data detected by the image detecting means, and a display means for displaying the result of the image processed by and from the image processing means. The image processing means comprises distortion measuring means for both measuring the amount of spatial coordinate distortion in the first image data from the correct coordinates, and storing data representing the distortion amount, first image memory means for storing the first image data, second memory means for storing second image data as the spatial distortion corrected first image data, first operating means for obtaining the address of each pixel in the first image data corresponding to each pixel address in the second image data, and second operating means for both obtaining, by an interpolating method and from the pixel intensity, the intensity of a pixel at a pixel address in the first imade data, and writing the obtained pixel intensity into a memory location at a predetermined pixel address in the second memory means.

According to the present invention, there is provided an X-ray imaging apparatus which can provide an image configured so as to closely approximate an image of an object under inspection or diagnosis by correcting the spatial distortion, through which apparatus an exact medical diagnosis and/or industrial inspection can be made.

Effective correction of spatial distortion accomodate, easy and effective composition of a single composite image. Accordingly, in reconstructing tomographic or stereoscopic images, the displayed image is approximate in configuration to the actual object, the exact dimensions of the target portions of the object of being obtained from the corrected image by measurement.

BRIEF DESCRIPTION OF THE DRAWINGS

FIG. 4 shows a diagram schematically illustrating an existing lattice point table used by the imaging apparatus;

FIGS. 5A and 5B show diagrams illustrating distortions of respective lattice points and their corrections;

FIG. 6 shows a vector diagram expressing a lattice point distortion;

FIG. 7 shows diagrams illustrating a relationship between a pixel intensity of the corrected image and that of a collected image;

FIG. 9 shows a block diagram illustrating, in detail, an image processor and a system controlled by the imaging apparatus shown in FIG. 8.

DETAILED DESCRIPTION OF THE PREFERRED EMBODIMENTS

The principles of the present invention will first be given.

Figure 1A:
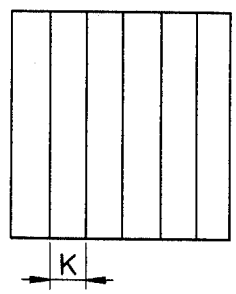
FIGS. 1A and 1B show models of a vertical stripe chart and a horizontal stripe chart as test charts used for an X-ray imaging apparatus which is an embodiment of the present invention.
Figure 1B:
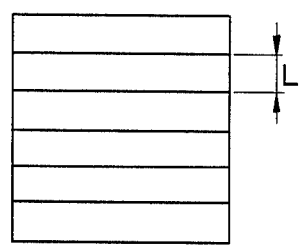

To operate an X-ray imaging apparatus according to the present invention, a test chart with a lattice-like pattern (hereinafter referred to as a lattice test chart or simply a test chart) is picked up before an object is picked up. A spatial distortion table and an existing lattice point table are prepared using the image of the picked up test chart, which contains spatial distortion. FIG. 1A shows a test chart with vertical stripes arranged with pitch K, these being partial constituents of the lattice test chart. FIG. 1B shows another test chart with horizontal stripes arranged with pitch L, which, likewise, are partial constituents of the lattice test chart.

Figure 2A:
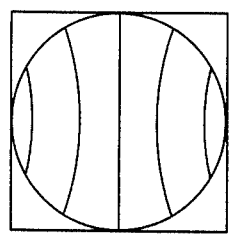
FIGS. 2A and 2B show images, displayed by the imaging apparatus, of the test charts shown in FIGS. 1A and 1B.
Figure 2B:
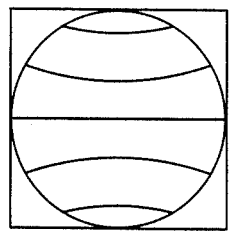
Figure 3A:
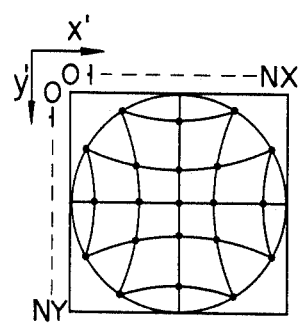
FIGS. 3A to 3C show respectively, an image of lattice points whose spatial distortion has not yet been corrected and which has been formed using the test charts of FIGS. 1A and 1B, an image of an actual object having not yet been passed through the detecting system of the imaging apparatus, and a corrected image.
Figure 3B:
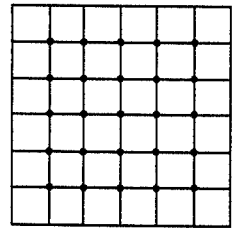
Figure 3C:
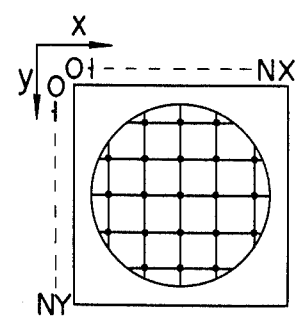

These test charts are picked up and imaged as shown in FIGS. 2A and 2B, respectively. As seen from the figures, these stripe patterns are distorted due to the spatial distortion which is an inherent characteristic of the detecting system of the imaging apparatus. The circular shape of each figure indicates that the X-ray detector is circular in shape. FIGS. 3A to 3C show a distorted image of test chart lattice points, an image of a lattice of the test chart before it is passed through the detecting system, and an image obtained when the distorted image is corrected. In the figures, vector $X=(x, y)$ indicates a picture element (pixel) address of the corrected image, and vector $X'=(x', y')$ indicates a pixel position of the distorted image. As can be seen, lattice points are arranged regularly in the lattice of the test chart (FIG. 3B), while they are arranged irregularly, due to spatial distortion, in the lattice of the distorted image (FIG. 3A). Further, in the distorted image, the number of lattice points is reduced because the pickup area of the lattice test chart is limited to the circular area defined by the X-ray detector.

Correction of the distorted image is made based on this distorted image. For image correction, a table, for indicating whether or not lattice points exist in the distorted image is prepared (FIG. 4). This table will be referred to as an existing lattice point table. In FIG. 4, a hatched portion indicates an area in which lattice points exist, denotations m and n indicating the coordinates of lattice points. A relationship between the distorted image of FIG. 3A and the corrected image of FIG. 3C is illustrated in FIGS. 5A and 5B. In the correct image of FIG. 5A, four lattice points are illustrated with vectors U(m, n), U(m+1, n), U(m, n+1), and U(m+1, n+1). As a generalization, the vector $U=(uX, uY)$, where uX is a, X-directional component. In the distorted image of FIG. 5B, another four lattice points are illustrated with vectors S(m, n), S(m+1, n), S(m, n+1), and S(m+1, n+1). The vector $S=(sX', sY')$, where sX' is an X'-directional component of the vector, and sY' a Y'-directional component. A conversion f from the image of FIG. 5A to that of FIG. 5B indicates that the image is distorted. The reverse conversion $f^{-1}$ from the image of FIG. 5B to that of FIG. 6A indicates that the distorted image is corrected. FIG. 6 shows distortion vectors of four lattice points D(m, n), D(m+1, n), D(m, n+1), and D(m+1, n+1). In the vector D, the X-directional component is dx, and the Y-directional component is dy. These vectors U(m, n), S(m, n), and D(m, n) are coupled to one another by the following equation.

$$D(m, n) = U(m, n) - S(m, n) \quad (1)$$

By using the equation (1), the distortion vectors at the other lattice points can also be calculated. The distortion vector at each lattice point can be resolved into the X- and Y-directional components. The X-directional vectors and the Y-directional vectors are stored into lattice point distortion vector tables. The pickup of the lattice test chart and the preparation of those vector tables is completed before the object is irradiated with X-rays.

Following the above operation, the object is subjected to X-rays, to thereby obtain an X-ray transmission image. The X-ray transmission image contains spatial distortion that must be corrected. It is, therefore, necessary to find a pixel position vector before correction, the gradation, e.g., the intensity of the pixel, being given to a pixel address vector after correction. To this end, by using the lattice point existing table and the lattice distortion vector table, pixel position vector X' before the correction which corresponds to a pixel address vector X after the correction, is obtained, the intensity of the pixel of this pixel position vector X' would be calculated from the distorted image.

Obtaining of the pixel position vector X' is, therefore, the first step. It is assumed here that the pixel address vector X in the corrected image (for example, an address within an area defined by four lattice points shown in FIG. 5A) exists with certainty within an area defined by four lattice points of the distorted image. With this assumption, it, is decided whether or not the coordinate vectors S(m, n), S(m+1, n), (m, n+1) and S(m+1, n+1) of the four lattice points in the distorted image which correspond to the coordinate vectors U(m, n), U(m+1, n), U(m, n+1) and U(m+1, n+1) of four lattice points containing the pixel address vector X, are within the hatched portion in the existing lattice point table shown in FIG. 4.

If all of the four lattice point vectors S(m, n), S(m+1, n), S(m, n+1) and S(m+1, n+1) are outside of the hatched portion in the existing lattice point table, there is no need for finding the position vector X'. When at most three of these four lattice point vectors are outside the hatched portion in the existing lattice point table, it is necessary to take the approximation of the lattice point vectors outside the hatched portion and then to calculate the position vector X' by using the approximated lattice point vectors and those inside the hatched portion.

If all of four lattice point vectors S(m, n), S(m+1, n), S(m, n+1) and S(m+1, n+1) are within the hatched portion, the location of the pixel position vector X' is obtained using the distortion vectors of the lattice points.

Assuming that the distortion vector in the pixel address vector X in the corrected image is D(X, Y) and that D(X, Y) is unknown, the pixel position vector X' in the distorted image is obtained from the equation (1) and given below $$X' = X - D(X, Y) \quad (2)$$

Since D (X, Y) is unknown, it is obtained by interpolating the distortion vectors D(m, n), D(m+1, n), D(m, n+1), and D(m+1, n+1). In this example, the interpolation based on the bilinear form is used for obtaining D(X, Y). In this example, the coordinates representative of the lattice points are $$U(m, n) = \{uX(m, n), uY(m, n)\}$$

and $$U(m+1, n) = \{uX(m+1, n), uY(m+1, n)\}.$$

A distance in the X direction between the adjacent lattice points is ΔP, and that in the Y direction is ΔQ.

Accordingly, the distortion vector D{uX(m, n), Y} at the position coordinates uX(m, n), Y in FIG. 6 is given as $$D\{uX(m, n), Y\} = D(m, n) + [y - uY(m, n)] \cdot 1/\Delta Q \cdot [D(m, n+1) - D(m, n)] \quad (b\ 3)$$

The distortion vector D{uX(m+1, n), Y} at the position coordinates [uX(m+1, n), Y} in FIG. 6 is given as $$D\{uX(m+1, n), Y\} = D(m+1, n) + [y - uY(m, n)] \cdot 1/\Delta Q \cdot [D(m, n+1) - D(m+1, n)] \quad (4)$$

Using the equations (3) and (4), the distortion vector D (X, Y) = {dX (X, Y), dY(X, Y)} at the position vector X = (X, Y) can be written as $$D(X, Y) = D\{uX(m, n), Y\} + [x - uX(m, n)] \cdot 1/\Delta P \cdot [D\{uX(m+1, n),Y\} - D\{uX(m, n), Y\}] \quad (5)$$

In this way, the pixel position vector X' in the distorted image corresponding to the pixel vector address X in the corrected image can be obtained using the equations (2) to (5).

Then, an intensity of the pixel at the pixel position vector X' is obtained. The pixel position vector X' does not always correspond to a pixel in the distorted image (pixel of the memory device). To cope with this, this position is resolved into an integer part (i, j) and a decimal part ($\alpha$, $\beta$), as shown in FIG. 7. x' and y' are given as $$x' = i + \alpha$$

$$y' = j + \beta$$

Pixel intensities at four address points containing the pixel position vector X' are expressed by C(i, j), C(i+1, j), C(i, j+1), C(i+1, j+1). By interpolating these pixel intensities through the bilinear form, the pixel intensity C(x', y') of the pixel position vector X' can be obtained and given by $$C(\alpha, j) = C(i, j) + \alpha[C(i+1, j) - C(i, j)] \quad (6)$$

$$C(\alpha, j+1) = C(i, j+1) + \alpha[C(i+1, j+1) \quad (7)$$

$$C(x', y') = C(\alpha, j) + \beta[C(\alpha, j+1) - C(\alpha, j)] \quad (8)$$

The spatial distortion can be corrected by using the pixel intensity C(x', y') of the pixel position vector X' thus obtained for the pixel intensity C(x, y) of the address vector X.

In the above example, four lattice points exist around the address vector X. If some of the four lattice points do not exist around the address vector X' they can be obtained by interpolating distortion vectors in the lattice area closest to the address vector X.

The correction procedure of the distorted image, based on the above principles of the present invention, can be summarized as follows.

1. The lattice point existing table and the lattice point distortion vector tables are prepared.
   1-1. The vertical and horizontal test charts are picked up and imaged.
   1-2. By using the images of the vertical and horizontal test charts, the position coordinates vector at the lattice points U(m, n), and the position coordinates vector at the lattice points in the distorted image S(m, n) are obtained.
   1-3. The existing lattice point table is prepared by raising flags when lattice points are found in the distorted image.
   1-4. The lattice point distortion vector table is prepared by obtaining the lattice point distortion vector D(m, n). 2. An object is picked up as a transmission image, and the transmission image is subjected to the correction of its spatial distortion.
   2-1. The object is picked up and the image data is collected and stored in the memory.
   2-2. By using the existing lattice table and the lattice distortion vector tables, calculation is conducted of the distortion vector D(x, y) of the pixel address vector X in the corrected image.
   2-3. The pixel position vector X' in the distorted image corresponding to the pixel address vector X is obtained.
   2-4. The pixel position vector X' is resolved into an integer part (i, j) and a decimal part ($\alpha$,$\beta$)
   2-5. The pixel intensity C(x', y') of the pixel position vector X' is calculated.
3. The pixel intensity C(x', y') is stored as the pixel intensity C(x, y) in the region for storing the corrected image.

An embodiment implementing the principles of the present invention thus far described will be described.

Figure 8:
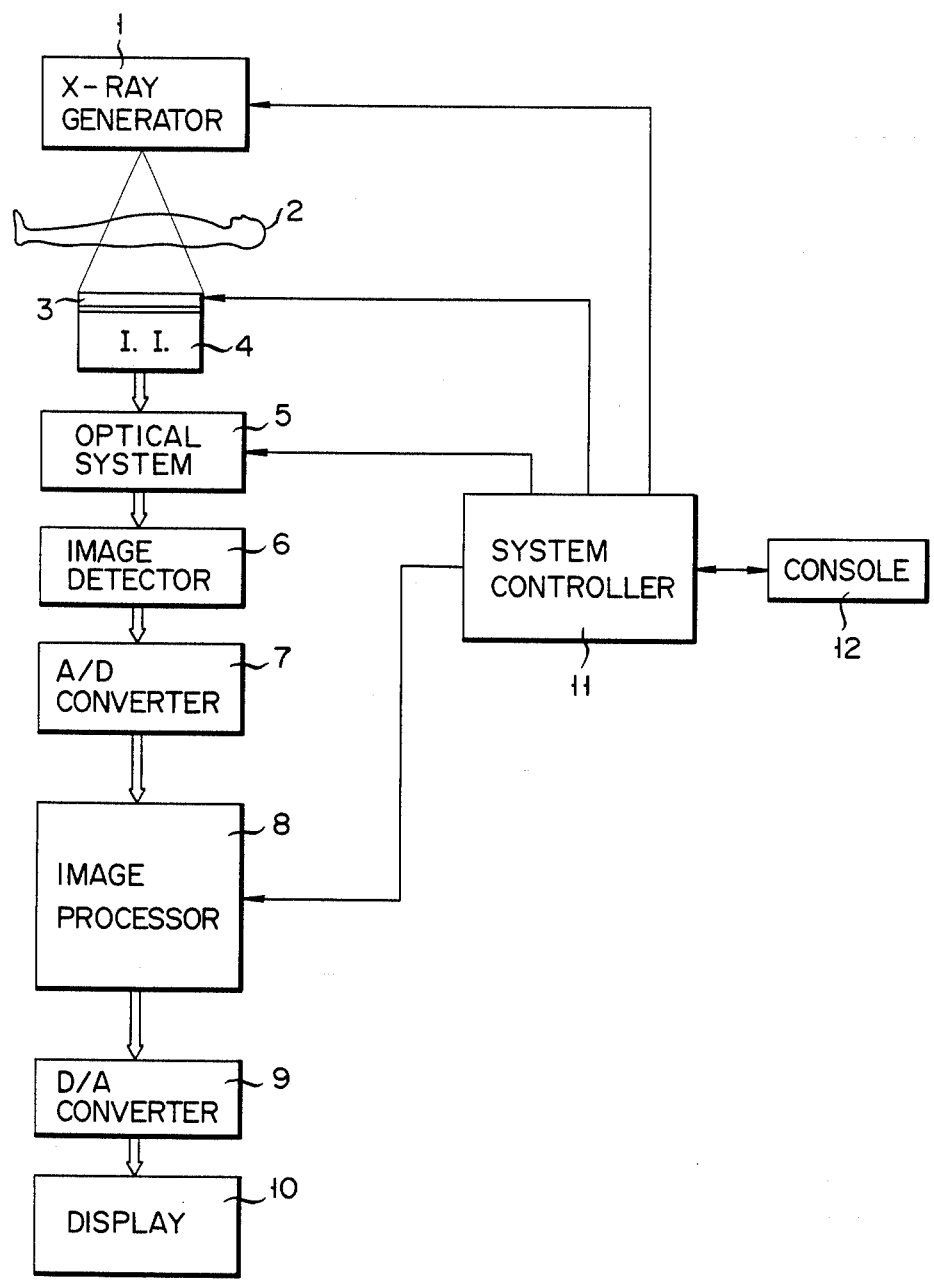
FIG. 8 is a block diagram illustrating an arrangement of an X-ray imaging apparatus according to an embodiment of the present invention.

FIG. 8 shows a block diagram of an X-ray imaging apparatus which is an embodiment of the present invention. In the figure, an X-ray generator 1 generates X-rays with which an object 2 is irradiated. A test chart setter 3 places a vertical stripe test chart, as shown in FIG. 2A, or a horizontal stripe test chart, as shown in FIG. 2B, in the X-ray irradiation field. An image intensifier (I.I.) 4 detects and amplifies an X-ray transmission image as obtained by X rays transmitted through the object 2 or the test chart, and then converts it into an optical image. An optical system 5 includes a lens system, an optical filter system a diaphragm system, etc. In the optical system 5, light rays emanating from the I.I. 4 are focused, guided and controlled in intensity. A two dimensional detector 6, as an image pickup tube, for example, converts the optical image passed through the optical system into a corresponding electrical signal. An A/D (analog to digital) converter 7 converts an analog signal from the two dimensional detector 6 into a digital signal. An image processor 8 includes an image processing controller, an image memory, and a processing section, as will be described later. A D/A (digital to analog) converter 9 converts the digital signal derived from the image processor 8 into an analog signal. An image display 10 visually displays an image of the object represented by the analog signal output from the D/A converter 9.

A system controller 11, containing a central processing unit (CPU), controls the operations of the X-ray generator 1, the test chart setter 3, the optical system 5 and the image processor 8. The system controller 11 will subsequently be described in detail. A console 12 contains a plurality of select keys which are used by an operator to select pick up conditions dependant on target portions in the object 2, and image processing modes, processing sequence and so on, which are already programmed and stored in the system controller 11.

The image processor 8 and the system controller 11 will be given referring to FIG. 9.

As shown in FIG. 9, the system controller 11 is coupled for control to the image processor 8, and is comprised of a CPU 20, a read only memory (ROM) 21, and either a random access memory (RAM) 22 or a read-/write memory. The image processor 8 comprises an image processing controller 30, an image memory 31, and a processing unit 32. The image processor, under control of the system controller 11, stores the image data output from the A/D converter 7 into the image memory 31 by way of the image processing controller 30, this image data being subjected to a predetermined processing in the processing section 32. The result of the operation is written into the RAM table 22 in the system controller 11, through the image memory 31, the D/A converter 9 or the image processing controller 30.

Figure 10:
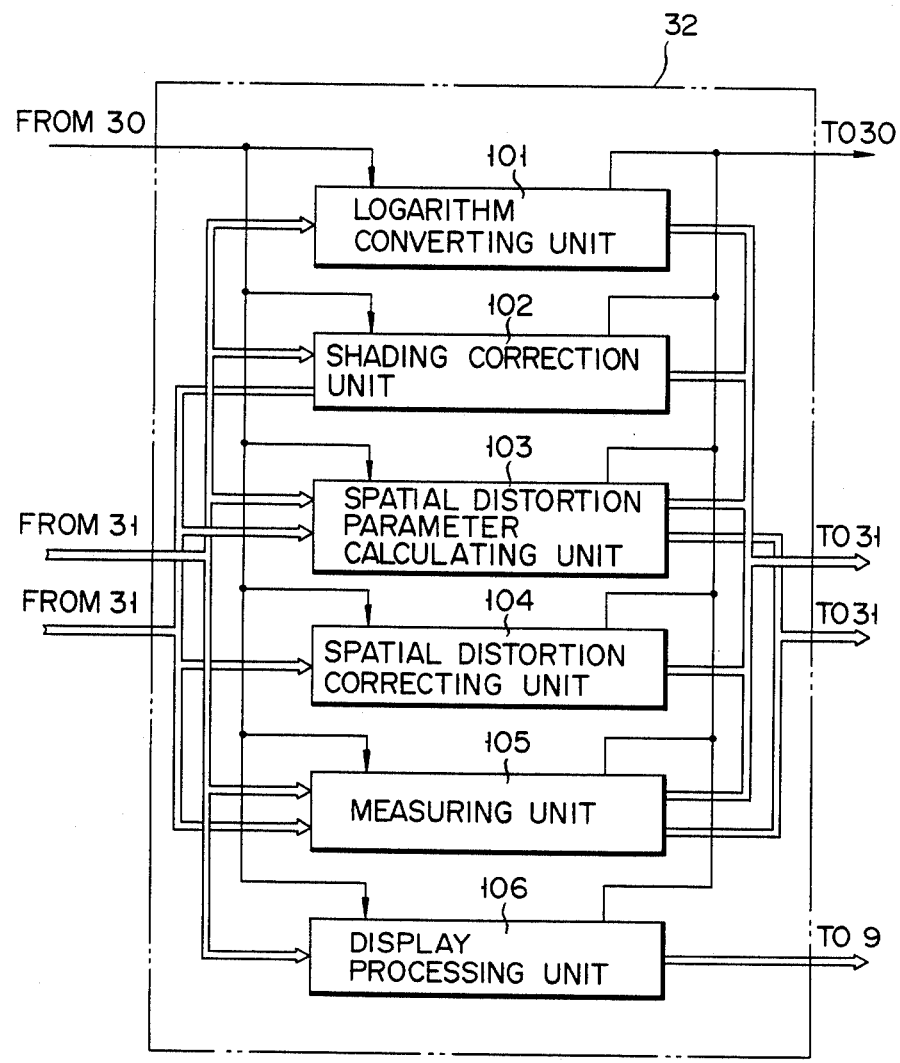
FIG. 10 shows a block diagram of a processing section of the image processor shown in FIG. 9.

FIG. 10 shows a configuration of the processing section 32.

In FIG. 10, a logarithm converting unit 101 is employed for logarithmic conversion, a shading correction unit 102 is for shading correction, and a spatial distortion parameter calculating unit 103 analyses a test chart image and prepares spatial distortion correcting parameters, i.e., the existing lattice point table and the lattice point distortion vector tables. These parameters are loaded into the RAM 22 of the system controller 11. A spatial distortion correcting unit 104 reads out the distortion parameters from the RAM table 22 and corrects the spatial distortion of the distorted image data of the object, and then finally stores the corrected image data into the image memory 31. A measuring unit 105 measures dimensions of the object, such as distance, area and volume. A display processing unit 106 gray level modulates the image data stored in the image memory 31, and applies the resultant image data to the D/A converter 9.

The image memory 31 serves as both a first memory means for storing the collected image data of the object, and a second memory means for storing the corrected image data. The spatial distortion correcting unit 104 serves as a first operating means for operating the pixel position vector X', and as a second operating means for operating the pixel intensity C(x', y').

The operation of the X-ray imaging apparatus thus arranged will be given.

Procedural steps to set the spatial distortion parameters (the existing lattice point table and the lattice point distortion vector tables) will be given.

When an operator operates a distortion parameter setting key on the console 12, the system controller 11 produces data representing X ray radiation condition data for the X-ray generator 1, data representing intensity attenuation for the optical system 5, and a processing sequence control signal for the image processor 8. The X-ray generator 1 is driven to radiate X rays, with the object 2 and the test chart not being placed in the X-ray irradiation field. The X-ray transmission image based on the X-ray irradiation is converted into an optical image by the I.I. 4. The optical image is attenuated, by the optical system 5, to a specified intensity, and then applied to the detector 6, e.g., the image pickup tube. The air pass data output from the detector 6 is analog data which is digitized by the A/D converter 7 and input to the image processor 8. The air pass data is passed through the image memory 31 and logarithm converted by the logarithm converting unit 101 and stored again into the memory location of a predetermined address in the image memory.

Then, the system controller 11 drives the test chart setter 3 to set the vertical test chart in the X-ray irradiation field. The vertical stripe image data, after logarithm conversion, is stored into a memory location of a predetermined address of the image memory 31, as in the case of the air pass data. The air pass image and the stripe image are then both input to the shading correction unit 102. These images are shade corrected by the shading correction unit 102 and stored into a predetermined memory area of the image memory 31.

The system controller 11 drives the test chart setter 3 to set the horizontal chart in the X-ray irradiation field. Then, the vertical stripe image data is shade corrected and stored into a predetermined memory location of the image memory 31, as in the case of the vertical stripe image data.

Then, the system controller 11 drives the image processing controller 30. The vertical and the horizontal stripe images are read out from the image memory 31 and input to the spatial distortion parameter calculating unit 103. The unit 103 computes the existing lattice point flags and the lattice point distortion vectors and stores them into the RAM 22 in the form of tables.

Following setting of the existing lattice point table and the lattice point distortion vector tables, the vertical and the horizontal stripe test charts are removed from the irradiation field, and the object 2 is set therein. Then, the operator operates the spatial distortion correcting key and an inspection start key on the console 11. Upon operation of these keys, the X-ray generator 1 generates X-rays in a predetermined sequence. The X-rays, after passing through the object 2, are incident on the I.I. 4 and converted into an amplified optical image which is detected by the two dimensional detector 6. Subsequently, as in the case of the test charts, the image data of the object is passed through the logarithm converting unit 101 and the shading correction unit 102, and the shade corrected image data is stored into a predetermined area of the image memory 31.

The stored image data of the object is then input to the spatial distortion correcting unit 104. This unit 104 reads out the existing lattice point table and the existing lattice point vectors from the RAM 22 and forms the spatial distortion corrected image by using the equations (2) to (8), the data of which image it then stores into a predetermined memory area of the image memory 31. If the dimensional measurement of the object is necessary, the spatial distortion corrected image data is read out and subjected to a determined dimension measurement by the measuring unit 105. If necessary, another image is formed and stored into a predetermined area of the memory 31. The measured value from the measuring unit 105 is stored into the RAM 22. The image data processed and then stored in the image memory 31 is input to the display processing unit 106 where it is gray scale modified and then applied to the D/A converter 9. The analog image signal from the converter 9 is then visually displayed by the display 10.

It should be understood that the present invention is not limited to the above-mentioned embodiment, but can be variously changed and modified within the scope of the present invention.

For example, the present invention can be applicable to industrial inspection using X-rays, and not merely to the medical diagnosis to which the present invention was applied in the above-mentioned embodiment. For the operations of the first and second operating means, the operating method based on the bilinear form was used for the reason that it enables the operation to be performed at high speed. It is evident that other suitable interpolation methods are available.

Further, the two test charts of vertical and horizontal stripes, may be substituted by a single test chart with a stripe pattern. In this case, the test chart is picked up and then turned 90°. Additionally, a test chart with lattice pattern of which the coordinates data is known, or of another appropriate pattern can be used.

What is claimed is:

1. An X-ray imaging apparatus having an X-ray generator for radiating X-rays toward an object, including means for detecting an image formed by X-rays transmitted through the object to obtain first image data, means for image processing the first data detected by the image detecting means, and display means for displaying the result of the image processing from the image processing means, the improvement wherein said image processing means comprises:

means for measuring the amount of spatial coordinate distortion data for each pixel of said first image data which corresponds to a real lattice point pattern;

means for storing said spatial coordinate distortion data;

means for calculating a first correction data at each pixel of spatial coordinate distortion based on said spatial coordinate distortion data;

first interpoltating means for obtaining a second correction data of spartial coordinate distortion at intermediate pixels between the pixels of calculated first correction data; and second interpolating means for obtaining pixel intensity data for the intermediate pixels of the second correction data based on the intensity of said first correction data.

2. The X-ray imaging apparatus according to claim 1, in which said storing means includes a test chart setting means for setting, in an image pickup region, a test chart whose spatial coordinates are known; distortion amount computing means for picking up said test chart placed in said pickup region by said test chart setting means to obtain first image data, and for obtaining an amount of distortion representing a coordinate relationship to the known spatial coordinates of said test chart; and distortion amount memory means for storing the distortion amount data obtained by said distortion amount computing means.

3. The X-ray imaging apparatus according to claim 2, in which said test chart setting means successively sets a test chart with a stripe pattern in two directions that differ by 90°.

4. The X-ray imaging apparatus according to claim 1, in which said test chart setting means sets a test chart with a lattice pattern.

5. The X-ray imaging apparatus according to claim 1, in which said first interpolating means performs the operation based on a bilinear form interpolation.

6. The X-ray imaging apparatus according to claim 1, in which said second operating means performs the operation based on a bilinear form interpolation.

7. The X-ray imaging apparatus according to claim 2, further comprising second memory means for storing second image data as the spartial distortion correction first image data, and dimension measuring means for measuring dimensions of the image readout from said second memory means.

8. The X-ray imaging apparatus according to claim 2, in which said image processing means further includes a shade measuring means for obtaining shading data from the image picked up when nothing is placed in the pickup region and for storing the shading data, and shade correcting means for correcting the picked up image data by using said shading data.

9. The X-ray imaging apparatus according to claim 1, in which there is an image intensifier for detecting a two dimensional image of transmitted X-rays and producing it as an optical image, and a television camera for picking up the optical image from said image intensifier.

* * * * *